United States Patent

Anderskewitz et al.

[11] Patent Number: 5,686,496
[45] Date of Patent: Nov. 11, 1997

[54] CHEMICAL COMPOUND, THE PREPARATION THEREOF AND ITS USE IN PHARMACEUTICAL COMPOSITIONS

[75] Inventors: Ralf Anderskewitz, Bingen; Kurt Schromm, Ingelheim; Ernst-Otto Renth, Ingelheim; Franz Birke, Ingelheim; Armin Fügner, Gau-Algesheim; Hubert Heuer, Schwabenheim; Christopher Meade, Bingen, all of Germany

[73] Assignee: Boehringer Ingelheim KG, Ingelheim am Rhein, Germany

[21] Appl. No.: 765,527

[22] PCT Filed: Jun. 3, 1995

[86] PCT No.: PCT/EP95/02113

§ 371 Date: Mar. 28, 1997

§ 102(e) Date: Mar. 28, 1997

[87] PCT Pub. No.: WO96/02496

PCT Pub. Date: Feb. 1, 1996

[51] Int. Cl.$^6$ ............ A61K 31/155; C07C 257/18

[52] U.S. Cl. ............ 514/637; 514/825; 514/826; 514/863; 514/903; 514/908; 564/247

[58] Field of Search ............ 564/247; 514/637, 514/825, 826, 863, 903, 908

[56] References Cited

FOREIGN PATENT DOCUMENTS 0 518 818  12/1992  European Pat. Off.
93/16036   8/1993   WIPO.

*Primary Examiner*—Peter O'Sullivan
*Attorney, Agent, or Firm*—Robert P. Raymond; Alan R. Stempel; Wendy E. Rieder

[57] ABSTRACT

The new compound of formula

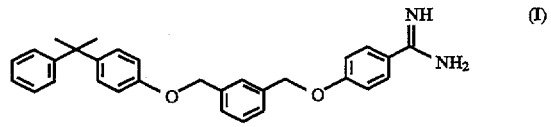

may be prepared by conventional methods and used therapeutically as an $LTB_4$-receptor antagonist.

5 Claims, No Drawings

CHEMICAL COMPOUND, THE PREPARATION THEREOF AND ITS USE IN PHARMACEUTICAL COMPOSITIONS

This application is a 371 of PCT/EP95/02113 filed Jun. 3, 1995.

The invention relates to the compound of formula (I)

Related compounds are known from WO 93/16036. They are described as $LTB_4$-antagonists and are suitable for therapeutic use in the corresponding indications.

It has been found that the compound of Formula 1 is characterised by its versatility in the therapeutic field. Particular mention should be made of those possible applications for which the $LTB_4$-receptor-antagonistic properties come into play. Example include, in particular: arthritis, asthma, chronic obstructive lung diseases, such as chronic bronchitis, psoriasis, ulcerative colitis, gastro or enteropathy induced by non-steroidal antilogistics, Alzheimers disease, shock, reperfusion damage/ischaemia, atherosclerosis and multiple sclerosis.

The new compounds may also be used to treat diseases or conditions in which the passage of cells from the blood through the vascular endothelium into tissue is of importance (such as metastasis) or diseases and conditions in which the combination of $LTB_4$ or another molecule (for example 12-HETE) with the $LTB_4$-receptor influences cell proliferation (such as chronic myelocytic leukaemia).

The new compounds may also be used in conjunction with other active substances, e.g. those which are used for the same indications or, for example, with antiallergics, secretolytics, $\beta_2$-adrenergics, steroids administered by inhalation, antihistamines and/or PAF-antagonists. The substances may be administered topically, orally, transdermally, nasally, parenterally or by inhalation.

The therapeutic or prophylactic dose depends not only on the potency on the individual compounds and the body weight of the patient, but also on the nature and gravity of the condition. For oral use the dose is between 10 and 500 mg, preferably between 20 and 250 mg. For inhalation a dosage of between 0.5 and 25, preferably between 2 and 20 mg of active substance is delivered to the patient.

The new compounds may be administered, e.g. as plain or coated tablets, capsules, lozenges, powders, granules, solutions, emulsions, syrups, inhalation aerosols, ointments or suppositories.

The Examples which follow illustrate some possible formulations for the preparations.

EXAMPLES OF FORMULATIONS

1. Tablets

| Composition: | |
|---|---|
| Active substance according to the invention | 20 parts by weight |
| Stearic acid | 6 parts by weight |
| Glucose | 474 parts by weight |

The ingredients are processed in the usual way to form tablets weighing 500 mg. If desired, the content of active substance increased or reduced and the quantity of glucose increased or reduced accordingly.

2. Suppositories

| Compositions: | |
|---|---|
| Active substance according to the invention | 100 parts by weight |
| Powdered lactose | 45 parts by weight |
| Cocoa butter | 1555 parts by weight |

The ingredients are processed in the usual way to form suppositories weighing 1.7 g.

3. Inhalation powder

Micronised powdered active substance (Compound of formula 1; particle size of about 0.5 to 7 μm) is packed into hard gelatine capsules in a quantity of 5 mg, optionally with the addition of micronised lactose. The powder is inhaled from conventional inhalers, e.g. according to DE-A 33 45 722.

The new compound exhibits a surprisingly superior effect, compared with the known $LTB_4$-antagonists. This is illustrated, for example, in the test results on the $LTB_4$-induced accumulation of neutrophiles in the mouse's ear. The $ED_{50}$ value of 0.05 mg/kg obtained is far lower than the values found for structurally similar compounds.

The new compound may be prepared by conventional methods:

Method 1

The amidoxime (II)

is catalytically hydrogenated.

The reaction is conveniently carried out in a polar solvent such as ethanol, glacial acetic acid or dimethylformamide at temperatures from ambient temperature up to 60° C. and at pressures from normal pressure up to 5 bar. Raney nickel or platinum may be used as catalyst.

The amidoxime used as starting material is obtained, for example, by reacting the corresponding nitrile with hydroxylamine.

Method 2

Compound I may be prepared from partial structures in which an amidine group is already present.

A compound of formula III is reacted with the phenol of formula IV or the phenol of formula V is reacted with a compound of formula VI:

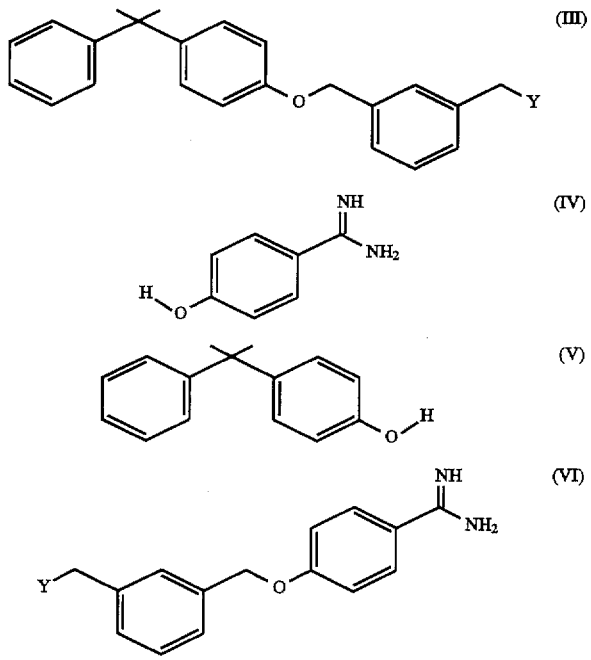

(wherein Y=halogen, preferably chlorine or bromine, or —O—SO$_2$—R$_2$, wherein R$_2$=alkyl, aryl)

The reaction is carried out in polar solvents such as acetonitrile, dimethylformamide and ethanol at temperatures of 60° to 120° C. in the presence of a base such as, for example, sodium methoxide or potassium carbonate.

The alkyl groups R$_2$ are usually groups with up to 6 carbon atoms. Aryl is preferably phenyl or tolyl.

The preparation of the new compound is described in more detail hereinafter.

EXAMPLE OF METHOD

Example 1

110.0 g of (4-{3-[4-(1-methyl-1-phenylethyl)-phenoxymethyl]-benzyloxy}phenyl)-carbaldoxime hydrochloride, prepared from (4-{3-[4-(1-methyl-1-phenylethyl)-phenoxymethyl]-benzyloxy}-phenyl)-carbonitrile with hydroxylamine hydrochloride and sodium carbonate in a boiling water/ethanol mixture (1:7), is hydrogenated in 2100 ml of methanol in the presence of 1 teaspoonful of Raney nickel at ambient temperature in about 3 hours. The catalyst is removed by suction filtration and the solution is filtered over silica gel. The methanol is distilled off, the residue is taken up in 2000 ml of ethyl acetate and extracted twice with 500 ml of water. The ethyl acetate is distilled off and the residue is recrystallised from 300 ml of ethanol. The product is dissolved in 200 ml of hot ethanol and slowly cooled overnight to ambient temperature. The crystals are collected by suction filtration, washed with 50 ml of cold ethanol and dried. Yield: 69 g; melting point 160° C.

We claim:

1. A compound of the formula

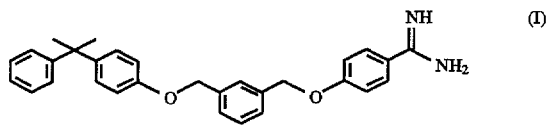

or a tautomer or pharmaceutically acceptable salt thereof.

2. A pharmaceutical composition comprising the compound of formula (I) as defined in claim 1 in association with pharmacologically acceptable galenic excipients, diluents and/or carriers.

3. A method for treating diseases which involve inflammatory and/or allergic processes which comprises administering to a subject suffering from the same a therapeutically effective amount of a compound in accordance with claim 1.

4. The method of claim 3 wherein the condition to be treated is selected from the group consisting of arthritis, asthma, chronic obstructive lung disease, psoriasis, ulcerative colitis, Alzheimer's disease, shock, atherosclerosis, multiple sclerosis, gastropathy induced by non-steroidal anti-inflammatories, metastasis and chronic myelocytic leukaemia.

5. A method for treating diseases in which LTB$_4$-receptor antagonistic therapy is required which comprises administering to a subject suffering from the same a therapeutically effective amount of a compound in accordance with claim 1.

* * * * *